United States Patent
Tu et al.

(12)

(10) Patent No.: US 6,217,576 B1
(45) Date of Patent: Apr. 17, 2001

(54) CATHETER PROBE FOR TREATING FOCAL ATRIAL FIBRILLATION IN PULMONARY VEINS

(75) Inventors: Hosheng Tu, Tustin; Weng-Kwen Raymond Chia, Irvine; Cary Hata, Tustin, all of CA (US)

(73) Assignee: Irvine Biomedical Inc., Irvine, CA (US)

( * ) Notice: Subject to any disclaimer, the term of this patent is extended or adjusted under 35 U.S.C. 154(b) by 0 days.

(21) Appl. No.: 09/283,039

(22) Filed: Apr. 1, 1999

Related U.S. Application Data (63) Continuation-in-part of application No. 09/100,176, filed on Jun. 18, 1998, now Pat. No. 5,913,856, which is a continuation-in-part of application No. 08/858,736, filed on May 19, 1997, now abandoned.

(51) Int. Cl.[7] ..................................................... A61B 17/36
(52) U.S. Cl. .............................................................. 606/41
(58) Field of Search .................................... 607/119, 122, 607/104, 105; 606/41

(56) References Cited

U.S. PATENT DOCUMENTS

| 5,313,943 | 5/1994 | Houser et al. . |
| 5,643,197 | 7/1997 | Brucker et al. . |
| 5,688,267 | * 11/1997 | Panescu et al. ....................... 607/122 |
| 5,876,398 | * 3/1999 | Mulier et al. ........................... 606/41 |

* cited by examiner

Primary Examiner—George R. Evanisko (57) ABSTRACT

An improved catheter system and methods for ablating cardiac tissues via a steerable ablation catheter having a liquid-permeable shaft, a liquid-permeable electrode, or a distal opening at its tip section with fluid infusion and irrigation for ablating intracardiac tissues by applying radiofrequency energy along with irrigated fluid in a pulmonary vein resulting in a controlled lesion for treating focal atrial fibrillation.

17 Claims, 4 Drawing Sheets

CATHETER PROBE FOR TREATING FOCAL ATRIAL FIBRILLATION IN PULMONARY VEINS

CROSS-REFERENCE TO RELATED APPLICATIONS

This is a continuation-in-part of application Ser. No. 09/100,176, filed on Jun. 18, 1998 now U.S. Pat. No. 5,913,556 which is a continuation-in-part of Ser. No. 08/858,736, filed on May 19, 1997 now abandoned.

FIELD OF THE INVENTION

The present invention generally relates to improved constructions for a catheter system. More particularly, this invention relates to catheters and methods for ablating cardiac tissues via a steerable ablation catheter having a liquid-permeable shaft, a liquid-permeable electrode, or a distal opening at its tip section with fluid infusion and irrigation means for ablating intracardiac tissues in a pulmonary vein resulting in a controlled lesion for treating focal atrial fibrillation.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart or in the pulmonary veins. The heart includes a number of normal pathways which are responsible for the propagation of electrical signals from the upper to the lower chambers necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to view the surrounding environment through the X-ray having contrast media and control the emission of energy to ablate the tissue within the heart or in the pulmonary veins.

Of particular interest to the present invention are radiofrequency (RF) ablation techniques which have been proven to be highly effective in tachycardia treatment while exposing a patient to minimal side effects and risks. RF catheter ablation is generally performed after conducting an initial mapping study where the locations of the arrhythmogenic site and/or accessory pathway are determined by the assistance of x-ray having contrast media. After a mapping study an ablation catheter is usually introduced to the target heart chamber and is manipulated so that the ablation tip electrode lies exactly at the target tissue site. RF energy or other suitable energy is then applied through the tip electrode to the cardiac tissue in order to ablate the tissue of arrhythmogenic site, the accessory pathway, or the focal atrial fibrillation. By successfully destroying that tissue, the abnormal signal patterns responsible for the tachycardia may be eliminated.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

A catheter utilized in the endocardial RF ablation is inserted into a major vein or artery, usually in the neck or groin area For focal AFib indications, a catheter is approached from the atrium to the ostium of a pulmonary vein. The tip section of a catheter is referred to hereby as the portion of that catheter shaft containing the electrode means which may be deflectable. The electrode means is to be positioned against the ostium of the pulmonary vein or inside the vein, whereby the electrode means having a firm wire, a ring electrode, an orthogonal electrode, a cap electrode, a guidewire, a mesh, or coil electrode means for lesion ablation.

The impedance usually rises at the tissue contact site when RF energy is delivered through an electrode. To create a deeper and larger controlled lesion, the surface of the tissue contact sites is preferred to maintain a proper temperature by a cooled fluid irrigation means to partially compensate for the temperature rise due to RF energy delivery.

The following U.S. patents have disclosed use of plurality of irrigation ports in different manners to cool the tissue contact surface. In practice, the fluid coming out of the irrigation ports may not evenly cover all the surface area of the electrode or the tissue to be ablated. Those patents are U.S. Pat No. 5,796,846 to Edwards et al., U.S. Pat No. 5,643,197 to Brucker et al., U.S. Pat No. 5,545,161 to Imran, U.S. Pat. No. 5,462,521 to Brucker et al., U.S. Pat. No. 5,437,662 to Nardella, U.S. Pat. No. 5,423,811 to Imram et al., U.S. Pat No. 5,409,000 to Imram, U.S. Pat. No. 5,348,554 to Imran et al., U.S. Pat. No. 5,334,193 to Nardella, and U.S. Pat No. 5,313,943 to Houser et al. However, none of the above-referred patents discloses an irrigation system of fluid through a liquid-permeable means to control the fluid effusion through a combination of the distal end and/or through the sides of the distal section.

The tip section of a catheter is referred to hereby as the portion of that catheter shaft containing at least one electrode. In one embodiment, a catheter utilized in the endocardial RF ablation is inserted into a major vein or artery, usually in the neck or groin area. The catheter is then guided into an appropriate chamber of the heart by appropriate manipulation through the vein or artery. The tip of a catheter must be manipulatable by a physician from the proximal end of the catheter, so that the electrodes at the tip section can be positioned against the tissue site to be ablated. The catheter must have a great deal of flexibility in order to follow the pathway of major blood vessels into the heart. It must permit user manipulation of the tip even when the catheter body is in a curved and/or twisted configuration. The tip section of a conventional electrophysiology catheter that is deflectable usually contains one large electrode about 4 nmm in length for ablation purpose. The lesion is generally not deep because of potential impedance rise of tissue in contact with the catheter electrode and the ablation time needs to be cut short. Even in the case of a conventional catheter with irrigation capabilities by utilizing a plurality of irrigation ports, the cooled fluid do not evenly and uniformly rinse the ablation electrodes.

The fluid irrigation means may also include delivery of contrast media to view the local tissue configuration with assistance of X-ray imaging. The prior art does not teach methods for controlling contrast media effusion from the distal end for viewing the forward tissue conduit, or from the sides of the shaft distal portion for viewing the relative location of the device inside a conduit, and/or a combination of contrast venting to see the whole environment. Therefore there is a need for a new and improved catheter for viewing the device and tissue configuration inside a conduit by fluid irrigation means including appropriate fluid control means.

SUMMARY OF THE INVENTION

In general, it is an object of the present invention to provide an improved catheter for even fluid infusion and irrigation of the exterior of the catheter through the distal end and/or through the sides of the shaft distal portion. This capability of even fluid infusion may be applicable to the drug delivery means to a tumor or cancer site. The capability of even fluid irrigation may be applicable to means of cooling off the tissue contact site due to impedance rise of the ablation electrodes. The capability of even fluid irrigation may also be applicable to means of providing contrast media for x-ray viewing or imaging. An ablation catheter with liquid-permeable tip section having at least one electrode can be used in effectively ablating the arrhythmogenic point or region of a patient. This catheter is particularly useful for treating a patient with focal atrial fibrillation (AFib) indications as a result of its cooled electrodes or delivery of controlled contrast media In one embodiment, a catheter probe comprises a catheter shaft having a shaft tip section, a shaft distal end, a shaft proximal end, and at least one lumen extending between the shaft distal end and the shaft proximal end, wherein the shaft distal end has a shaft opening that is connected to and in communication with the at least one lumen. A handle is attached to the shaft proximal end, wherein the handle has a cavity. The catheter probe further comprises fluid irrigation means for providing fluid to the distal tip section, wherein the fluid irrigation means is externally connected to a fluid supply source. Furthermore, the catheter probe comprises fluid control means at the shaft distal end for controlling flow rate of the fluid irrigation means through the shaft opening.

The fluid control means of said catheter probe may comprise a fluid deployment mechanism at the handle and a movable cap that is distal to the shaft distal end, wherein the fluid deployment mechanism may cause the cap to move toward the shaft distal end and matches and blocks said shaft opening to shut off flow of the fluid irrigation means at a non-deployed state. In one alternate embodiment, the movable cap may be tapered or in other proper special shape to fit and match the opening of the distal end. The movable cap may be deployed by the fluid deployment mechanism to move distally away from the shaft opening of the shaft distal end to allow fluid flow of the fluid irrigation means. The fluid deployment mechanism may also cause the movable cap to rotate or tip for controlling the fluid flow out of the shaft opening.

In a preferred embodiment, a catheter probe may further comprise at least one electrode mounted on the shaft tip section, wherein the entire shaft tip section comprises a flexible liquid-permeable plastic material, wherein said flexible liquid-permeable plastic material surrounds the at least one electrode on all sides and underneath the at least one electrode except for an outer surface of the electrode; wherein the liquid-permeable plastic material is adapted for fluid infusion, effusion and irrigation of the shaft tip section when the fluid deployment mechanism is at a non-deployed state; wherein fluid is effused out of the liquid-permeable plastic material, and wherein fluid irrigates and cools the at least one electrode by evenly covering and rinsing the at least one electrode so that an impedance rise at the contact site between the at least one electrode and tissue is substantially reduced.

In an alternate embodiment, a catheter probe may further comprise at least one electrode mounted at the shaft tip section, wherein the at least one electrode is made of liquid-permeable material, wherein the liquid-permeable electrode is adapted for fluid infusion, effusion and irrigation of the at least one electrode when the fluid deployment mechanism is at a non-deployed state; wherein fluid is effused out of the liquid-permeable electrode, and wherein fluid irrigates and cools the at least one electrode by evenly covering and rinsing the at least one electrode so that an impedance rise at the contact site between the at least one electrode and tissue is substantially reduced.

The pore or hole sizes of the substrate, including liquid-permeable shaft, liquidpermeable electrode, and liquid-permeable movable cap, range from 5 to 1000 microns. This liquid-permeable substrate with a pore size range of 5 to 1000 microns is also typically known as the microporous substrate. It is another object to provide a catheter with a shaft made of flexible liquid-permeable plastic material.

A fluid source is positioned at one end of the catheter for supplying a fluid flow through the lumen or a fluid conduit of said catheter shaft to the tip section which is constructed of a liquid-permeable substrate, such as a flexible liquid-permeable plastic material, a liquid-permeable electrode, a liquid-permeable movable cap, or a liquid-permeable distal opening hole or holes. Therefore at ablation time, the tip section with at least one electrode is positioned against the tissues to be ablated. The fluid is continuously or intermittently supplied through the liquid-permeable shaft or the at least one liquid-permeable electrode to evenly cover and rinse the electrode so that the impedance rise at the contact site is substantially reduced. In still another embodiment, a liquid-permeable metal electrode is employed so that the fluid will flow out of the liquid-permeable electrode while delivering RF energy. The porosity of said liquid-permeable metal electrode is appropriate for fluid irrigation of a fluid flow rate preferably in the range of 5 cc/min to 20 cc/min. By cooling off the electrode during RF energy delivery will result in optimal ablation efficiency and a desired deep and large lesion.

The ablation catheter further comprises a steering mechanism at the handle for controlling the deflection of said distal tip section having a liquid-permeable shaft, liquid-permeable electrodes, or a liquid-permeable movable cap. Usually a rotating ring or a push-pull plunger is employed in the steering mechanism. In another embodiment, the steerable ablation catheter comprises a bidirectional deflection or multiple curves deflection of the tip section having a liquid-permeable distal shaft portion. One end of the steering wire is attached at certain point of the tip section of said catheter shaft. The other end is attached to the steering mechanism at the handle. The steering mechanism on a steerable catheter or device is well known to those who are skilled in the art.

A fluid conveying lumen or a fluid conduit is associated with the elongate catheter shaft, and is preferably disposed within the catheter shaft along the longitudinal axis thereof The lumen is adapted to communicate with a fluid supply source to convey fluid from the source and through the lumen/conduit to be discharged through the liquid-permeable tip section and diffuse out of the tip section containing at least one electrode.

The invention also comprises a method and system for controlling the flow rate of fluid through the lumen or fluid conduit to optimize the cooling effect of the energy delivering electrode of the catheter or to optimize X-ray viewing with delivery of contrast media. The control system preferably regulates the flow rate based on signals representative of the temperature of the catheter tip and/or tissue impedance.

At least one electrical conductor which is secured to the at least one electrode passes through the lumen of the catheter shaft and the interior void of the handle and is thereafter secured to a contact pin of the connector secured at the proximal end of the handle. Therefrom, the electrical conductor is connected to an external RF generator for ablation operations and/or to an EKG monitor for recording and display of the endocardial or epicardial electrical signal. The catheter probe system comprises a RF current generator, wherein the RF current generator is adapted for delivering RF current to the at least one electrode through an electrical conductor.

In an additional embodiment, the ablation system filter comprises a temperature sensing and closed-loop temperature control mechanism for the electrode having at least one temperature sensor mounted at the tissue contact site of the at least one electrode. The location of the temperature sensor is preferably in the very proximity of or on one of the electrodes. In a still further embodiment, a method for operating an ablation catheter further comprises a programmed temperature control mechanism for independently controlling the delivery of RF energy of each electrode of the ablation catheter.

In a particular embodiment, the length of at least one electrode is 4 mm or longer. The material for the electrodes may consist of conductive metals such as platinum, iridium, gold, silver, stainless steel, Nitinol, or an alloy of their mixture. In a still further embodiment, the tip section of the catheter shaft comprises at least one electrode that is formed of a liquid-permeable conducting material. The liquid-permeable conducting metal and its fabrication to form an electrode is well known to those who are skilled in the art. In another embodiment, the electrodes to be placed outside of and wrapped around the liquid-permeable tip section of the catheter shaft of this invention are formed of a flexible metal mesh or coil.

In order to provide increased torsional rigidity to the catheter shaft, the shaft material preferably comprises a polymeric tube having a Durometer in the range from 30D to 90D, usually from 40D to 65D. Preferably, the shaft has a composite structure including a base layer of a relatively low Durometer material, a stiffening layer, for example, metal braid or coil, and an outer layer comprising the biocompatible polymeric material or the material that may render itself biocompatible by surface treatment. To enhance biocompatibility, the catheter shaft further comprises surface coating of heparin or anti-thrombotic substrate on the surface of the catheter shaft. It is hypothesized that the coated heparin forms a barrier, while not releasing heparin from said surface, between the blood and the catheter surface to enhance biocompatibility during electrophysiology procedures.

A method for operating a steerable ablation catheter system having at least one electrode at the tip section having fluid irrigation means and fluid control means, within a heart chamber comprises (a) percutaneously introducing the catheter probe through a body opening to the cavity or the tubular organ of a patient; (b) intimately contacting the at least one electrode on a tissue of the cavity or the tubular organ; (c) deploying the fluid control means for controlling flow rate of the fluid irrigation means through the shaft opening; (d) applying RF energy to the at least one electrode through the electrical conductor; and (e) withdrawing the catheter probe from the patient.

The catheter system of the present invention has several significant advantages over known catheters or ablation techniques. In particular, the evenly cooled electrode of a steerable ablation catheter of this invention may result in a controlled deeper and larger lesion that is highly desirable in the focal AFib treatment. Furthermore, the fluid irrigation means and fluid control means of the present invention may control the delivery of contrast media for X-ray viewing through the distal opening, through the sides of the distal shaft section or a combination of both.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE PREFERRED EMBODIMENTS

Figure 1:
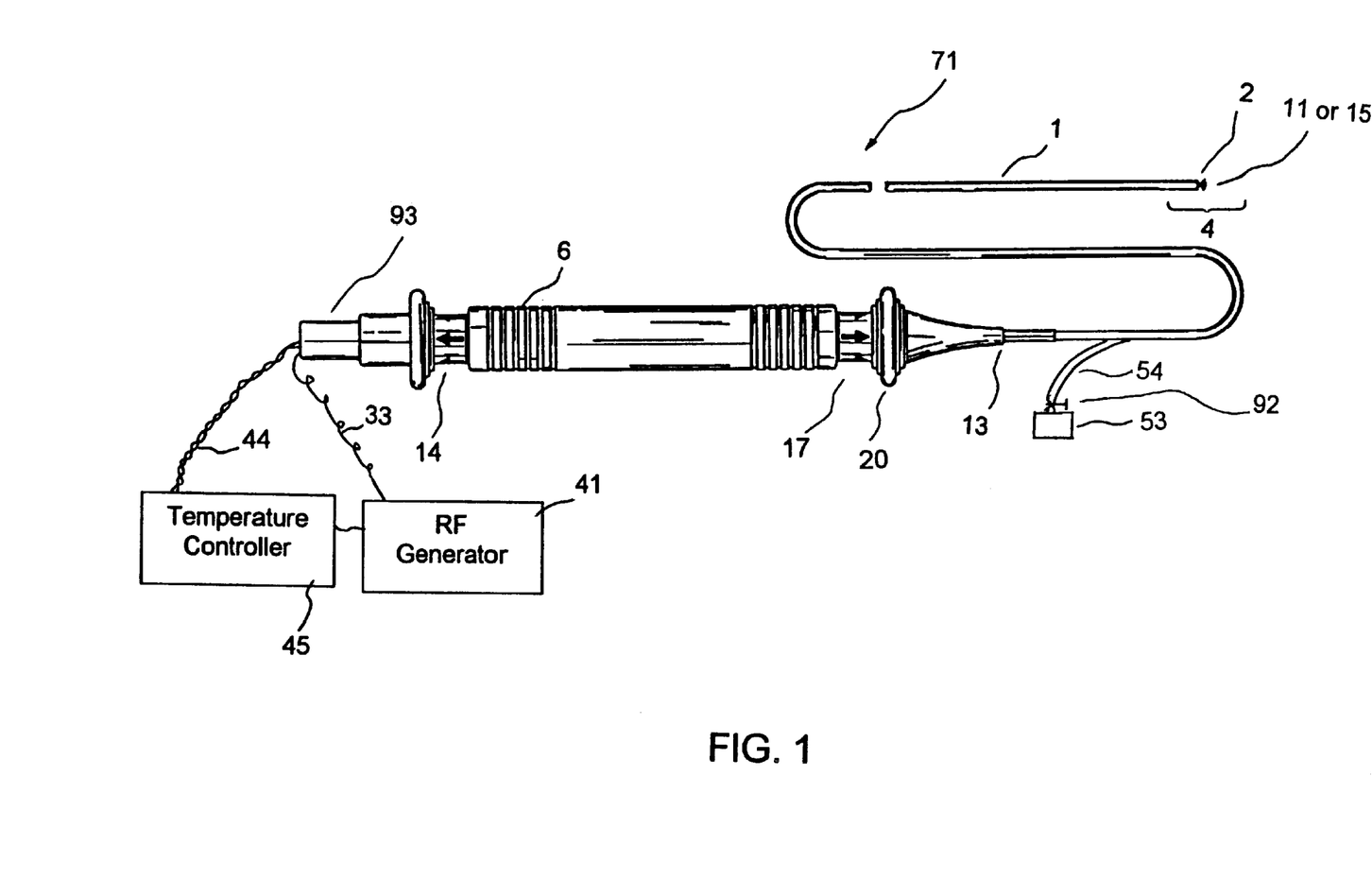
FIG. 1 is an overall view of a catheter probe having a liquid-permeable distal portion constructed in accordance with the principles of the present invention.

FIG. 1 shows a perspective view of the catheter having fluid irrigation means and fluid control means. An ablation catheter 71 constructed in accordance with the principles of the present invention comprises a catheter shaft 1 having a distal tip section 4, a distal end 2, a proximal end 13, and at least one lumen 91 extending therebetween. The catheter comprises a fluid infusion mechanism 54 of the fluid irrigation means close to the proximal end 13 of the catheter shaft 1. A control valve 92 is secured to the fluid infusion mechanism 54 that is externally connected to a fluid supply source 53 having a pump or other pressurizing means. A handle 6 is attached to the proximal end 13 of said catheter shaft 1.

The connector 93 secured at the proximal end of the catheter probe 71, is part of the handle section 6. The handle has one steering mechanism 17. The steering mechanism 17 is to deflect the tip section 4 of the catheter shaft 1 for catheter maneuvering and positioning. By pushing the front plunger 20 of the handle 6, the tip section of the catheter tip section deflects to one direction. By pulling the front plunger 20, the tip section returns to its neutral position. In another embodiment, the steering mechanism 17 at the handle 6 comprises means for providing a plurality of deflectable curves on the distal tip section 4 of the catheter.

Figure 2:
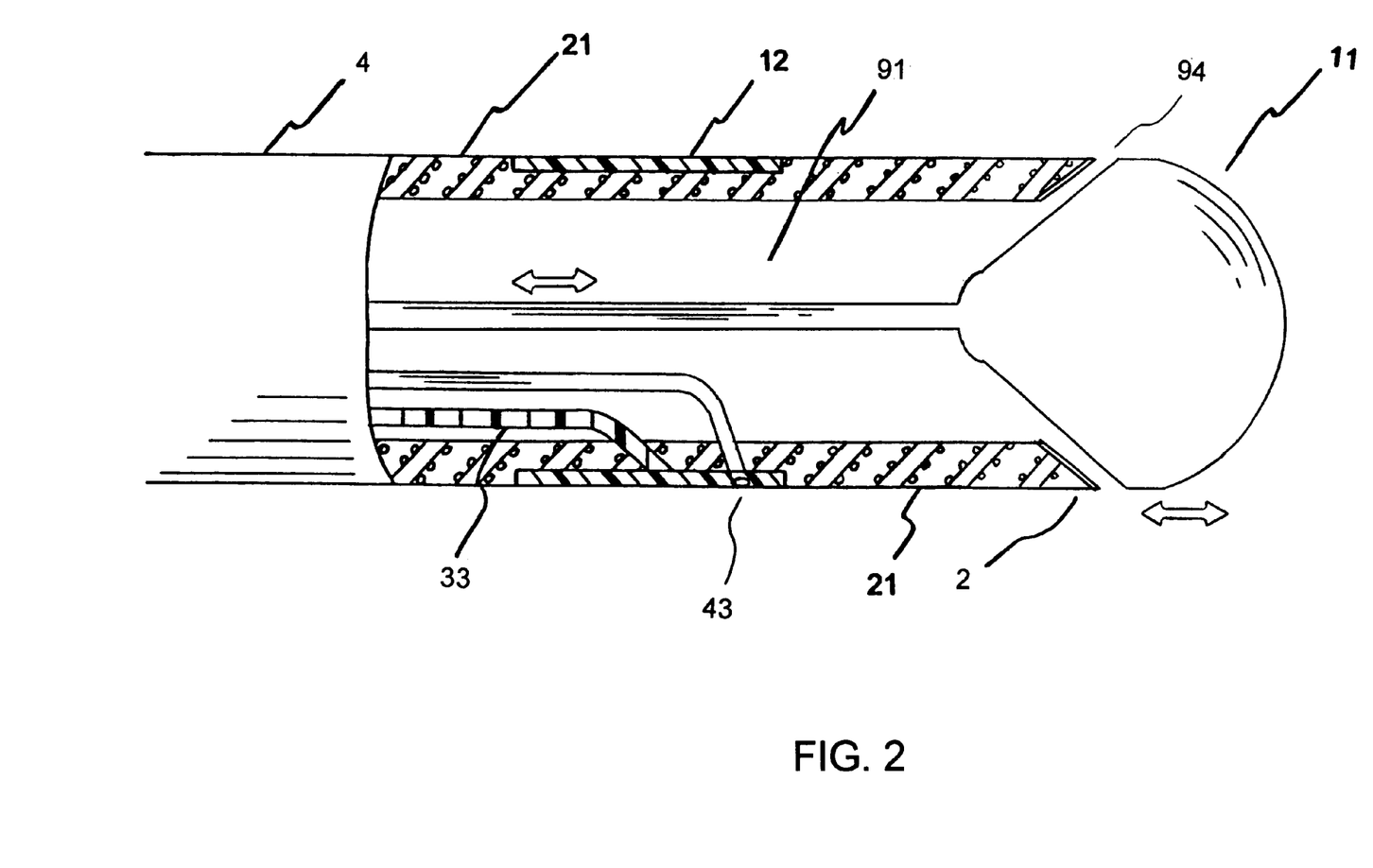
FIG. 2 is a close-up view of the distal section of the catheter probe comprising a liquid-permeable shaft with fluid irrigation and fluid control means.

FIG. 2 shows a close-up view of the distal section of the catheter probe with a liquid-permeable shaft, wherein the pore sizes of the liquid-permeable shaft range from 5 to 1000 microns. This substrate with a pore size range of 5 to 1000 microns is also typically known as the microporous substrate. In one embodiment, the catheter shaft 21 of the tip section 4 of this preferred embodiment is constructed of a flexible liquid-permeable plastic material. Since the catheter shaft is made of plastic material, it is flexible and deflectable to be used as a medical device. The porosity of said plastic material is such that the fluid flow rate from the fluid infusion mechanism 10 may be between approximately 5 ml/min to 20 ml/min. The tip section 4 of the catheter shaft 1 comprises a movable cap 11 and at least one electrode 12. The at least one electrode 12 and optionally the movable cap 11 are formed of a conducting material. In one other embodiment, the at least one electrode is a metal mesh or a metal coil securely wrapped outside of the catheter shaft 21 of the catheter system.

The catheter probe 71 comprises fluid control means for controlling flow rate of the fluid irrigation means through the shaft opening 94 at the shaft distal end 2. In one embodiment, the fluid control means comprises a fluid deployment mechanism 14 at the handle 6 and a movable cap 11 that is distal to the shaft distal end 2, wherein the fluid deployment mechanism causes the movable cap 11 to move toward the shaft distal end 2 and positions itself into said shaft opening 94 to shut off flow of the fluid irrigation means at a non-deployed state, and wherein the movable cap 11 is deployed by the fluid deployment mechanism to move distally away from the shaft opening 94 of the shaft distal end 2 to allow fluid flow out of the shaft opening 94.

In one embodiment, the entire shaft tip section 4 comprises a flexible liquid-permeable plastic material, wherein said flexible liquid-permeable plastic material surrounds the at least one electrode 12 on all sides and underneath the at least one electrode except for an outer surface of the electrode; wherein the liquid-permeable plastic material is adapted for fluid infusion, effusion and irrigation of the shaft tip section 4 when the fluid deployment mechanism is at a non-deployed state; wherein fluid is effused out of the liquid-permeable plastic material, and wherein fluid irrigates and cools the at least one electrode 12 by evenly covering and rinsing the at least one electrode so that an impedance rise at the contact site between the at least one electrode and tissue is substantially reduced.

Figure 3:
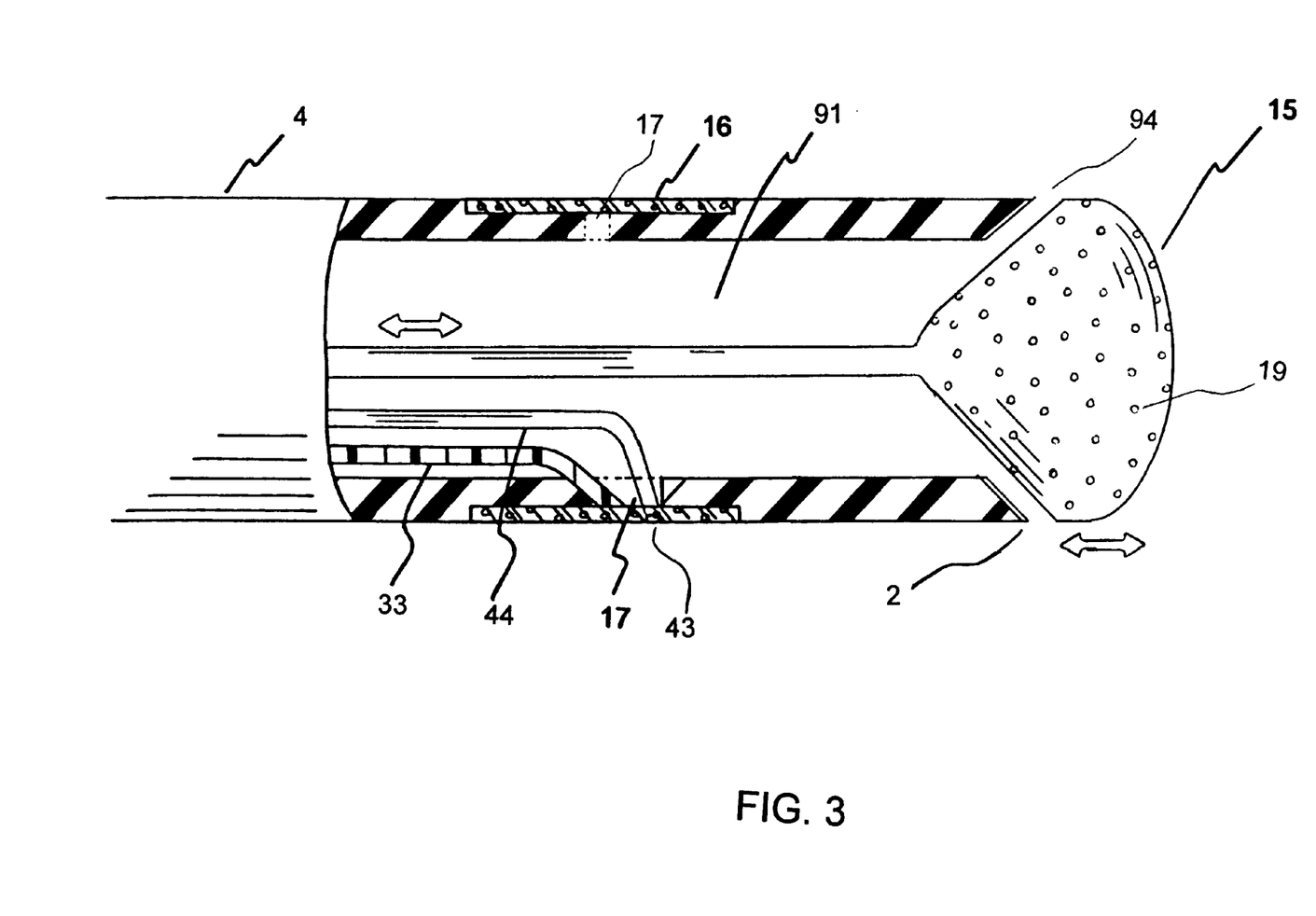
FIG. 3 is a close-up view of the distal section of the catheter probe comprising liquid-permeable metal electrodes with fluid irrigation means and fluid control means.

FIG. 3 shows a cross-sectional view of the tip section having at least one liquid-permeable electrode with at least one temperature sensor 43. The at least one electrode 16 and optionally the movable cap 15 are constructed of conductive liquid-permeable metal. To convey the fluid through the liquid-permeable electrodes to the exterior of the catheter, a connecting passage 17 is provided for the fluid to flow into and through the at least one electrode 16. The fluid may flow into movable cap 15 through the permeable surface 19 of said cap 15. The liquid-permeable electrode is adapted for fluid infusion, effusion and irrigation of the at least one electrode when the fluid deployment mechanism is at a nondeployed state; wherein fluid is effused out of the liquid-permeable electrode 16, and wherein fluid irrigates and cools the at least one electrode by evenly covering and rinsing the at least one electrode so that an impedance rise at the contact site between the at least one electrode and tissue is substantially reduced.

The at least one electrode, and optionally the movable cap, has an insulated conducting wire 33 secured to the electrode 12, 16, which passes through the lumen 91 of the catheter shaft 1 and is secured to a contact pin of the connector 93 at the proximal end of the handle 6. The conducting wire 33 from the connector end is externally connected to an EKG for diagnosis or to a RF generator 41 during an electrophysiology ablation procedure. Therefrom, the RF energy is transmitted through the conducting wire to the electrode and delivered the energy to the target tissue.

A temperature sensor 43, either a thermocouple means or a thermister means, is constructed at the proximity of the electrodes 12, 16, or the movable cap 11 or 15 to measure the tissue contact temperature when RF energy is delivered. The temperature sensing wire 44 from the thermocouple or thermister is connected to one of the contact pins of the connector 93 and externally connected to a transducer and to a temperature controller 45. The temperature reading is thereafter relayed to a closed-loop control mechanism to adjust the RF energy output. The RF energy delivered is thus controlled by the temperature sensor reading or by a pre-programmed control algorithm.

The catheter of this invention is to provide fluid communication and commensurate flow of fluid originating from a reservoir 53 to the exterior surface of the shaft distal section through a liquid-permeable substrate, either a flexible liquid-permeable plastic shaft, a liquid-permeable electrode, or a liquid-permeable cap at its distal tip section, which directs the fluid flow from inside the catheter shaft over the exterior surface of the catheter shaft to provide a fluid protective layer surrounding the electrode to minimize temperature elevation of the electrode with biological tissues. Similarly, contrast media can be delivered through said liquid-permeable substrate for X-ray viewing and imaging.

Figure 4:
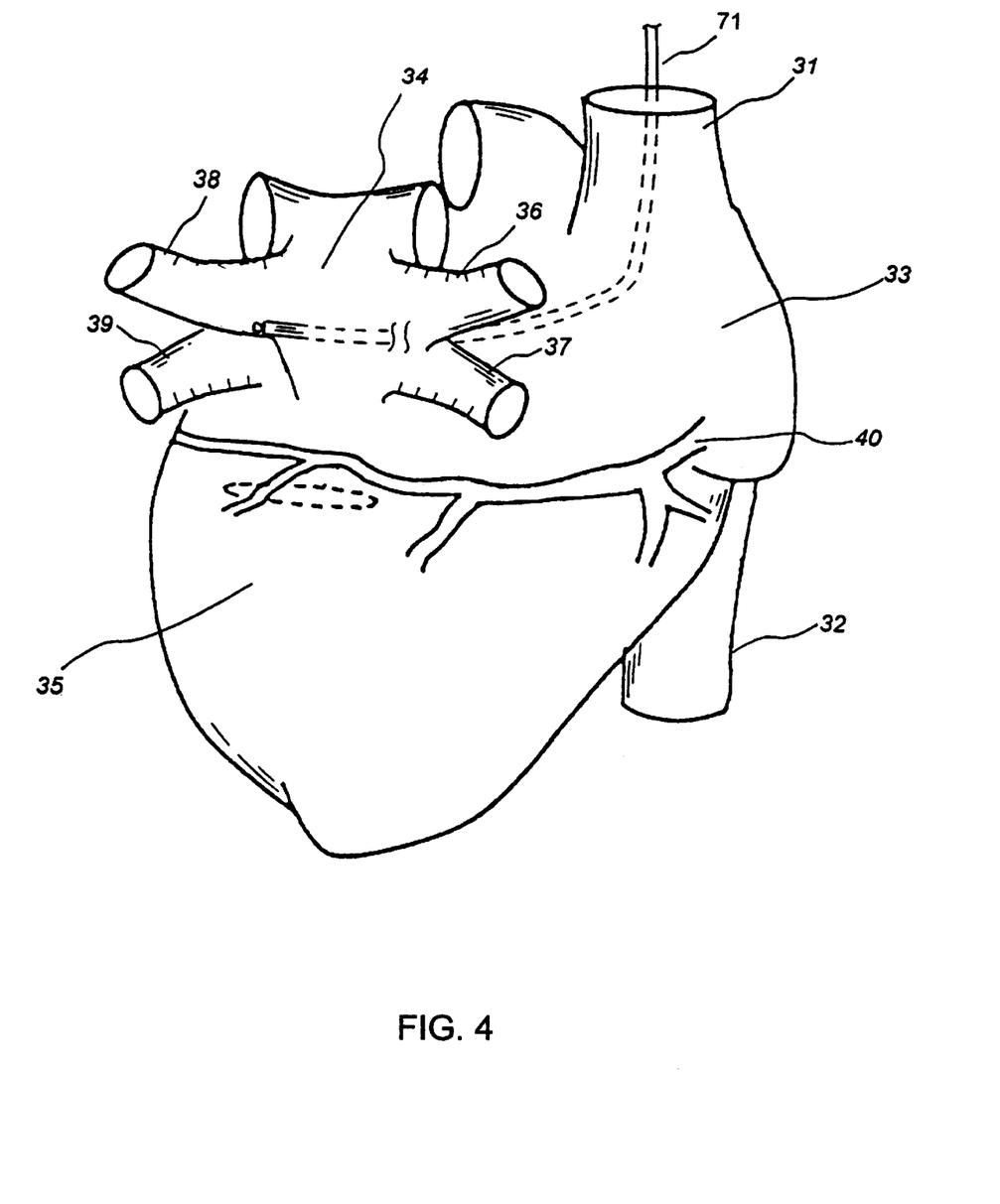
FIG. 4 is a perspective view of a catheter probe of the present invention when placed inside one pulmonary vein of the left atrium for focal atrial fibrillation treatment.

FIG. 4 shows a perspective view of a catheter probe of the present invention when placed inside one pulmonary vein of the left atrium for paroxysmal atrial fibrillation treatment. To better illustrate the application of the present invention, a human heart is shown in FIG. 4. Blood returning from superior vena cava 31 or inferior vena cava 32 flows back to the right atrium 33. A coronary sinus 40 is part of the coronary artery system to provide nutrient to the epicardial heart tissue, wherein the heart also comprises a left atrium 34, a left ventricle 35 and a right ventricle. A catheter probe 71 of the present invention passing through the superior vena cava 31 into the right atrium 33. The catheter With a delivery sheath or a guiding catheter passes through the septal into the left atrium 34 for focal AFib treatment by using a standard trans-septal procedure. A normal people has four pulmonary veins: right superior pulmonary vein 36, right inferior pulmonary vein 37, left superior pulmonary vein 38, and left inferior pulmonary vein 39. In one example, a catheter probe 71 is inserted into the left atrium while its distal tip section is inserted into the left superior pulmonary vein 38. After the distal portion of the catheter probe 71 is inside the vein 38, the movable cap 11 or 15 is deployed to control and regulate the flow or flow rate through the liquid-permeable substrate, including liquid-permeable shaft, liquid-permeable electrode, or liquid-permeable cap for cooling the electrode or for delivering contrast media for enhanced X-ray imaging.

In one embodiment, a method for operating a catheter probe 71 within a cavity or a tubular organ of a patient is illustrated, wherein the catheter probe comprises a catheter shaft having a shaft tip section 4 that comprises at least one electrode 12, 16 mounted on the shaft tip section, a shaft distal end 2, a shaft proximal end 13, and at least one lumen 91 extending between the shaft distal end and the shaft proximal end, wherein the shaft distal end has a shaft opening 94 that is connected to and in communication with the at least one lumen 91; a handle 6 attached to the shaft proximal end 13, wherein the handle has a cavity; fluid irrigation means for providing fluid to the distal tip section 4, wherein the fluid irrigation means is externally connected to a fluid supply source 53; fluid control means at the shaft distal end for controlling flow rate of the fluid irrigation means through the shaft opening 94; and a RF current generator 41, wherein the RF current generator is adapted for delivering RF current to the at least one electrode through an electrical conductor 33. The method comprises the steps of (a) percutaneously introducing the catheter probe through a body opening to the cavity or the tubular organ of a patient; (b) intimately contacting the at least one electrode on a tissue of the cavity or the tubular organ; (c) deploying the fluid control means for controlling flow rate of the fluid irrigation means through the shaft opening; (d) applying RF energy to the at least one electrode through the electrical conductor; and (e) withdrawing the catheter probe from the patient.

In another embodiment, an alternate method for operating a catheter probe within a cavity or a tubular organ of a patient is illustrated, wherein the catheter probe comprising a catheter shaft having a shaft tip section that comprises at least one electrode mounted on the shaft tip section, a shaft distal end, a shaft proximal end, and at least one lumen extending between the shaft distal end and the shaft proximal end, wherein the shaft distal end has a shaft opening that is connected to and in communication with the at least one lumnen; a handle attached to the shaft proximal end, wherein the handle has a cavity; fluid irrigation means for providing fluid to the distal tip section, wherein the fluid irrigation means is externally connected to a fluid supply source; and fluid control means at the shaft distal end for controlling flow rate of the fluid irrigation means through the shaft opening. The method comprises the steps of (a) percutaneously introducing the catheter probe through an opening to the cavity or the tubular organ of a patient; (b) intimately contacting the at least one electrode on a tissue of the cavity or the tubular organ; (c) deploying the fluid deployment mechanism for controlling flow rate of the fluid irrigation means through the shaft, wherein fluid may effuse out of the catheter shaft from the shaft opening, or from a liquid-permeable shaft portion; and (d) withdrawing the catheter probe from the patient.

From the foregoing, it should now be appreciated that an improved ablation catheter having a liquid-permeable shaft and an fluid infusion capability has been disclosed for ablation procedures, including endocardial, epicardial, or body tissue and drug delivery to a tumor or cancer site. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter probe comprising:
   a catheter shaft having a shaft tip section, a shaft distal end, a shaft proximal end, and at least one lumen extending between the shaft distal end and the shaft proximal end, wherein the shaft distal end has a shaft opening that is connected to and in communication with the at least one lumen;
   a handle attached to the shaft proximal end, wherein the handle has a cavity;
   a fluid supply source;
   fluid irrigation means for providing fluid to the shaft distal end, wherein the fluid irrigation means is externally connected to the fluid supply source; and
   fluid control means for controlling flow rate of the fluid irrigation means through the shaft opening at the shaft distal end, wherein the fluid control means comprises a fluid deployment mechanism at the handle and a movable cap that is distal to the shaft distal end, wherein the fluid deployment mechanism causes the movable cap to move toward the shaft distal end and positions said movable cap into said shaft opening to shut off flow of the fluid irrigation means at a non-deployed state, and wherein the movable cap is deployed by the fluid deployment mechanism to move distally away from the shaft opening of the shaft distal end to allow fluid flow out of the shaft opening.

2. The catheter probe as in claim 1 further comprising at least one electrode mounted on the shaft tip section, wherein the entire shaft tip section comprises a flexible liquid-permeable plastic material, wherein said flexible liquid-permeable plastic material surrounds the at least one electrode on all sides and underneath the at least one electrode except for an outer surface of the electrode; wherein the liquid-permeable plastic material is adapted for fluid infusion, effusion and irrigation of the shaft tip section when the fluid deployment mechanism is at a non-deployed state; wherein fluid is effused out of the liquid-permeable plastic material, and wherein fluid irrigates and cools the at least one electrode by evenly covering and rinsing the at least one electrode so that an impedance rise at the contact site between the at least one electrode and tissue is substantially reduced.

3. The catheter probe as in claim 1 further comprising at least one electrode mounted at the shaft tip section, wherein the at least one electrode is made of liquid-permeable material, wherein the liquid-permeable electrode is adapted for fluid infusion, effusion and irrigation of the at least one electrode when the fluid deployment mechanism is at a non-deployed state; wherein fluid is effused out of the liquid-permeable electrode, and wherein fluid irrigates and cools the at least one electrode by evenly covering and rinsing the at least one electrode so that an impedance rise at the contact site between the at least one electrode and tissue is substantially reduced.

4. The catheter probe as in claims 2 or 3 further comprising a RF current generator, wherein the RF current generator is adapted for delivering RF current to the at least one electrode through an electrical conductor.

5. The catheter probe as in claim 4 further comprising at least one temperature sensor mounted on the at least one electrode, wherein the catheter probe is equipped with a closed-loop temperature controller, and wherein the at least one temperature sensor is adapted for providing temperature sensing signals to the closed-loop temperature controller for controlling the RF current delivery.

6. The catheter probe of claim 2, wherein the at least one electrode is made of a coil material or a mesh material.

7. The catheter probe as in claims 2 or 3, wherein the at least one electrode is made of material selected from the group consisting of Nitinol, gold, stainless steel, silver, platinum, iridium, and an alloy of their mixtures.

8. The catheter probe as in claims 2 or 3 further comprising a steering mechanism at the handle for controlling deflection of the shaft tip section.

9. A method for operating a catheter probe within a cavity or a tubular organ of a patient, the catheter probe comprising a catheter shaft having a shaft tip section that comprises at least one electrode mounted on the shaft tip section, a shaft distal end, a shaft proximal end, and at least one lumen extending between the shaft distal end and the shaft proximal end, wherein the shaft distal end has a shaft opening that is connected to and in communication with the at least one lumen; a handle attached to the shaft proximal end, wherein the handle has a cavity; a fluid supply source; fluid irrigation means for providing fluid to the shaft distal end, wherein the fluid irrigation means is externally connected to the fluid supply source; fluid control means at the shaft distal end for controlling flow rate of the fluid irrigation means through the shaft opening; wherein the fluid control means comprises a fluid deployment mechanism at the handle and a movable cap that is distal to the shaft distal end, wherein the fluid deployment mechanism causes the movable cap to move toward the shaft distal end and positions said movable cap into said shaft opening to shut off flow of the fluid irrigation means at a non-deployed state, and wherein the movable cap is deployed by the fluid deployment mechanism to move distally away from the shaft opening of the shaft distal end to allow fluid flow out of the shaft opening; an electrical conductor; and a RF current generator, wherein the RF current generator is adapted for delivering RF current to the at least one electrode through the electrical conductor;

the method comprising the steps of:
(a) percutaneously introducing the catheter probe through a body opening to the cavity or the tubular organ of a patient; (b) intimately contacting the at least one electrode on a tissue of the cavity or the tubular organ; (c) deploying the fluid control means for controlling flow rate of the fluid irrigation means through the shaft opening; (d) applying RF energy to the at least one electrode through the electrical conductor; and (e) withdrawing the catheter probe from the patient.

10. The method for operating a catheter probe within a cavity or a tubular organ of a patient as in claim 9, further comprising at least one electrode mounted on the shaft tip section, wherein the entire shaft tip section comprises a flexible liquid-permeable plastic material, wherein said flexible liquid-permeable plastic material surrounds the at least one electrode on all sides and underneath the at least one electrode except for an outer surface of the electrode; wherein the liquid-permeable plastic material is adapted for fluid infusion, effusion and irrigation of the shaft tip section when the fluid deployment mechanism is at a non-deployed state; wherein fluid is effused out of the liquid-permeable plastic material, and wherein fluid irrigates and cools the at least one electrode by evenly covering and rinsing the at least one electrode so that an impedance rise at the contact site between the at least one electrode and tissue is substantially reduced.

11. The method for operating a catheter probe within a cavity or a tubular organ of a patient of claim 9, wherein the at least one electrode is made of liquid-permeable material, wherein the liquid-permeable electrode is adapted for fluid infusion, effusion and irrigation of the at least one electrode when the fluid deployment mechanism is at a non-deployed state; wherein fluid is effused out of the liquid-permeable electrode, and wherein fluid irrigates and cools the at least one electrode by evenly covering and rinsing the at least one electrode so that an impedance rise at the contact site between the at least one electrode and tissue is substantially reduced.

12. The method for operating a catheter probe within a cavity or a tubular organ of a patient as in claim 9, further comprising at least one temperature sensor mounted on the at least one electrode, wherein the catheter probe is equipped with a closed-loop temperature controller, and wherein the at least one temperature sensor is adapted for providing temperature sensing signals to the closed-loop temperature controller for controlling the RF current delivery.

13. The method for operating a catheter probe within a cavity or a tubular organ of a patient of claim 9, wherein the catheter probe further comprising a steering mechanism at the handle for controlling deflection of the shaft tip section.

14. A method for operating a catheter probe within a cavity or a tubular organ of a patient, the catheter probe comprising a catheter shaft having a shaft tip section that comprises at least one electrode mounted on the shaft tip section, a shaft distal end, a shaft proximal end, and at least one lumen extending between the shaft distal end and the shaft proximal end, wherein the shaft distal end has a shaft opening that is connected to and in communication with the at least one lumen; a handle attached to the shaft proximal end, wherein the handle has a cavity; a fluid supply source; fluid irrigation means for providing fluid to the shaft distal end, wherein the fluid irrigation means is externally connected to the fluid supply source; and fluid control means at the shaft distal end for controlling flow rate of the fluid irrigation means through the shaft opening, wherein the fluid control means comprises a fluid deployment mechanism at the handle and a movable cap that is distal to the shaft distal end, wherein the fluid deployment mechanism causes the movable cap to move toward the shaft distal end and matches said shaft opening to shut off flow of the fluid irrigation means at a non-deployed state, and wherein the movable cap is deployed by the fluid deployment mechanism to move distally away from the shaft opening of the shaft distal end to allow fluid flow out of the shaft opening;

the method comprising the steps of:
(a) percutaneously introducing the catheter probe through an opening to the cavity or the tubular organ of a patient; (b) intimately contacting the at least one electrode on a tissue of the cavity or the tubular organ; (c) deploying the fluid deployment mechanism for controlling flow rate of the fluid irrigation means through the shaft, wherein fluid may effuse out of the catheter shaft from the shaft opening, or from a liquid-permeable shaft portion; and (d) withdrawing the catheter probe from the patient.

15. The method for operating a catheter probe within a cavity or a tubular organ of a patient as in claim 14, wherein the entire shaft tip section comprises a flexible liquid-permeable plastic material, wherein said flexible liquid-permeable plastic material surrounds the at least one electrode on all sides and underneath the at least one electrode except for an outer surface of the electrode; wherein the liquid-permeable plastic material is adapted for contrast media fluid infusion, effusion and irrigation of the shaft tip section when the fluid deployment mechanism is at a non-deployed state; wherein contrast media fluid is effused out of the liquid-permeable plastic material, and wherein contrast media fluid irrigates the at least one electrode to be viewed by an X-ray imaging.

16. The method for operating a catheter probe within a cavity or a tubular organ of a patient of claim 14, further comprising at least one electrode mounted at the shaft tip section, wherein the at least one electrode is made of liquid-permeable material, wherein the liquid-permeable electrode is adapted for fluid infusion, effusion and irrigation of the at least one electrode when the fluid deployment mechanism is at a non-deployed state; wherein contrast media fluid is effused out of the liquid-permeable electrode, and wherein contrast media fluid irrigates the at least one electrode to be viewed by an X-ray imaging.

17. The method for operating a catheter probe within a cavity or a tubular organ of a patient of claim 14, wherein the catheter probe further comprising a steering mechanism at the handle for controlling deflection of the shaft tip section.

* * * * *